United States Patent

Blake-Coleman

Patent Number: 5,383,349
Date of Patent: Jan. 24, 1995

[54] DENSITOMETER

[75] Inventor: Barrie Blake-Coleman, Salisbury, United Kingdom

[73] Assignee: Public Health Laboratory Service Board, London, England

[21] Appl. No.: 834,235

[22] PCT Filed: Aug. 17, 1990

[86] PCT. No.: PCT/GB90/01306
§ 371 Date: Feb. 18, 1992
§ 102(e) Date: Feb. 18, 1992

[87] PCT Pub. No.: WO91/02963
PCT Pub. Date: Mar. 7, 1991

[30] Foreign Application Priority Data

Aug. 17, 1989 [GB] United Kingdom ............ 8918766
Dec. 29, 1989 [GB] United Kingdom ............ 8929330

[51] Int. Cl.⁶ .................................... G01N 9/00
[52] U.S. Cl. ............................. 73/32 A; 73/433; 73/580
[58] Field of Search .......... 73/32 A, 24.05, 24.06, 73/433, 580

[56] References Cited

U.S. PATENT DOCUMENTS

| | | | |
|---|---|---|---|
| 3,295,360 | 3/1967 | Dimeff | 73/24.05 |
| 3,745,811 | 7/1973 | Dure et al. | 73/32 A |
| 4,429,564 | 2/1984 | Ikeda et al. | 73/32 A |
| 4,628,739 | 12/1986 | Bruggen et al. | 73/32 A |
| 4,872,335 | 10/1989 | Tsuruoka et al. | 73/32 A |

FOREIGN PATENT DOCUMENTS

| | | |
|---|---|---|
| 0221467 | 5/1987 | European Pat. Off. |
| 0801757 | 9/1958 | United Kingdom |
| 1146764 | 3/1969 | United Kingdom |

*Primary Examiner*—John E. Chapman
*Attorney, Agent, or Firm*—Browdy and Neimark

[57] ABSTRACT

A fluid densitometer is constructed using loudspeaker technology. The loudspeaker diaphragm carries a fluid sample chamber. The increased mass loading causes a shift in resonant frequency of the loudspeaker when driven in positive feedback. With suitable calibration the shift in frequency provides a measure of the density of the fluid sample. In a modification, two loudspeakers are mounted back to back with the opposing diaphragms defining a sample chamber.

7 Claims, 4 Drawing Sheets

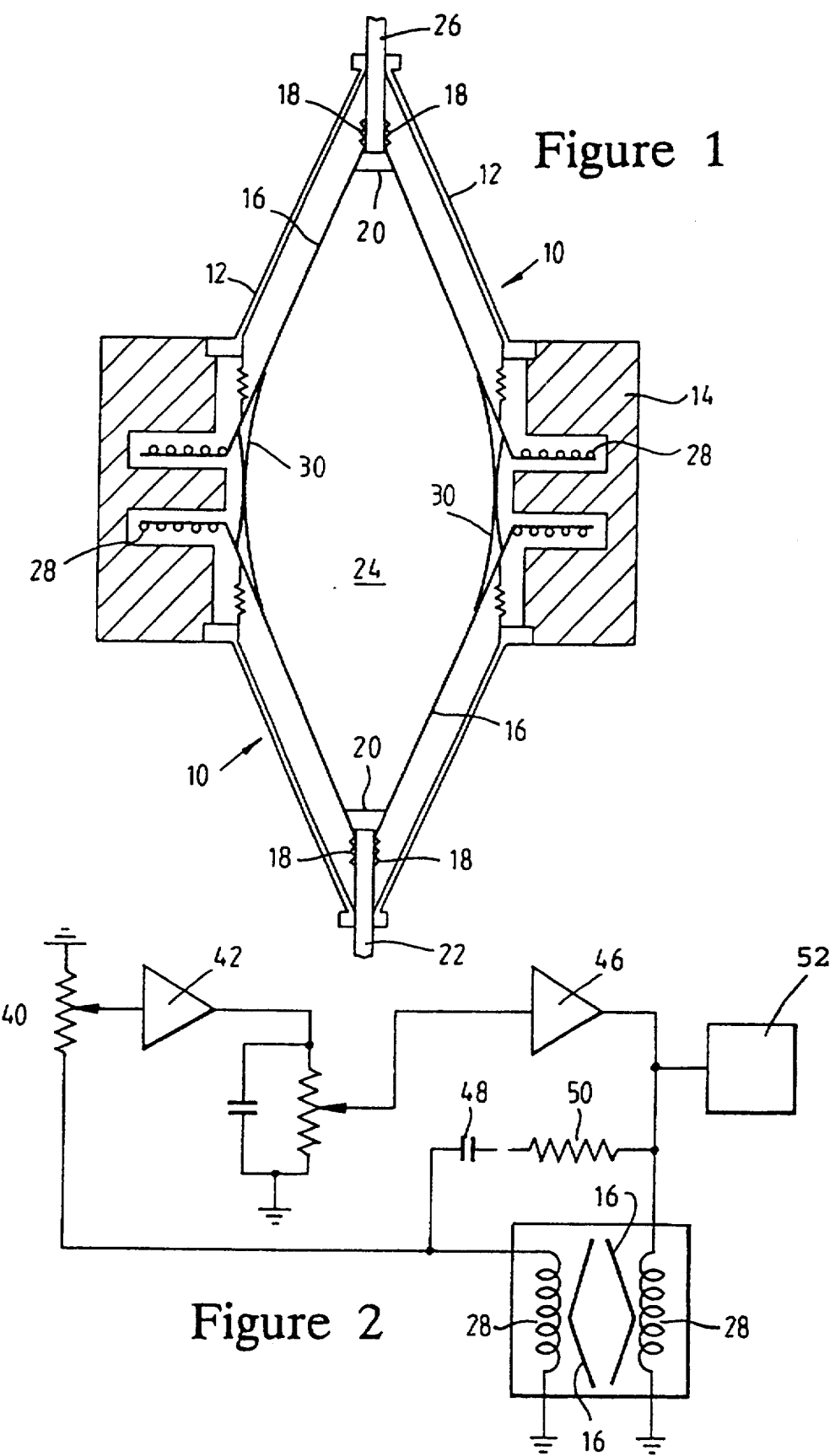

DENSITOMETER

BACKGROUND OF THE INVENTION

This invention relates to fluid densitometers.

Acoustic resonance densitometers are now well known for use in measuring fluid density. Typically, a sample chamber is formed as part of a mechanical resonator system which is driven into self resonance by incorporating appropriate transducers and an electronic amplifier in a closed loop positive feedback circuit. The sample chamber is often a straight or U shaped tube through which the sample flows.

The commercially available systems are expensive even in the case of low resolution instruments. This is to a large extent because the mechanical resonators are difficult and expensive to make, it being necessary to control the acoustic properties within very close limits. There are typically large numbers of machining and heat treatment steps with high reject rates in quality control.

It is an object of this invention to provide a liquid densitometer which is of low cost yet which offers a reasonable resolution and reproducibility in measurements.

SUMMARY OF THE INVENTION

Accordingly the present invention consists in one aspect in a liquid densitometer comprising a base; a diaphragm suspended in the base for vibrational movement relative thereto; an electromagnetic coupling means having cooperating elements mounted respectively on the base and the diaphragm and having an electrical such that vibrational movement of the diaphragm is excited on the application of a periodic electrical signal thereto; a sample chamber for receiving a fixed volume of a liquid sample and associated with the diaphragm to load massively the diaphragm in accordance with the density of the sample. The frequency of vibration of the diaphragm is measured and compared with a predetermined frequency of vibration at a known massive loading of the diaphragm to obtain therefrom a measure of the density of the fluid sample.

Preferably, there is provided a positive feedback loop connected with the electrical terminal and serving in use to drive the diaphragm into vibrational resonance.

Advantageously, the positive feedback loop includes automatic gain control to ensure vibration of the diaphragm at constant amplitude.

In another aspect, the present invention consists in a liquid densitometer, comprising a base; a concave diaphragm; a suspension connected between the outer periphery of the diaphragm and the base to provide for generally axial vibrational movement of the diaphragm relative to the base; and electrical coil means provided on the diaphragm; a magnet supported on the base and positioned to generate a magnetic field at the coil; a driver for applying an electrical signal to the coil to excite vibrational movement; and a sample chamber for receiving a fixed volume of a liquid sample and associated with the diaphragm to load massively the diaphragm in accordance with the density of the sample. The frequency of vibration of the diaphragm is measured and compared with a predetermined frequency of vibration at a known massive loading of the diaphragm to obtain a measure of the density of the sample.

In a further aspect, the present invention consists in a fluid densitometer comprising a base; a diaphragm having a drive axis; an annular suspension disposed circumferentially of said drive axis and acting between the diaphragm and the base to provide for axial vibration of the diaphragm; a pair of coils provided on the diaphragm at respective opposite sides of the annular suspension; A magnet supported on the base and positioned to generate a magnetic field at each of said coils; an amplifier connected to receive a feedback signal from one of the coils and connected with another of the coils to provide a drive signal thereto, the arrangement being such as to excite a resonant frequency of axial vibration of the diaphragm; and a sample chamber for receiving a fixed volume of a liquid sample and associated with the diaphragm to load massively the diaphragm means in accordance with the density of the sample. A frequency meter is connected with at least one of the coils to determine the frequency of vibrational movement of the diaphragm which is compared with a predetermined frequency of vibration at a known massive loading of the diaphragm means to obtain a measure of the density of the sample.

This invention enables use to be made of existing loud speaker technology.

It has surprisingly been found that by providing a fluid sample chamber to load massively the diaphragm of an otherwise conventional loudspeaker, a measure of fluid density can be obtained from the shift in resonant frequency of the diaphragm when driven in positive feedback.

In a preferred arrangement, two loudspeakers are mounted essentially back-to-back so that the respective diaphragms vibrate in unison. The effect of massively loading the diaphragms will be to reduce the resonant frequency so it is preferable to use high frequency loudspeakers or "tweeters". Because the sample chamber may be subject to pressure variations, it will be necessary to ensure that the chamber is of fixed volume when filled. Thus, in the case where the two diaphragms themselves serve to define the sample chamber, the opposing peripheries of the diaphragm are bonded together—by a locking ring for example so that a fixed volume chamber is provided with the diaphragms being incapable of independent displacement under pressure. In an alternative arrangement, a separate, fixed volume sample chamber is provided between the two diaphragms.

The choice of materials for the sample chamber is important and should satisfy the criteria of low density, low thermal coefficient of expansion and a small and linear stress characteristic. Examples of possible materials are thin gauge ferro-nickel alloys (typically Nispan C), polymer coated aluminium alloys and certain polymers such as PTFE. The suspension will be selected to minimize variations in stiffness with, for example, temperature or time.

It should be understood that whilst densitometers according to the present invention can be constructed using actual loudspeakers, large scale manufacture would more sensibly employ components designed for the specific purpose. Nevertheless, considerable reliance can be placed on existing, proven loudspeaker technology enabling large economies in design and manufacture as compared with existing fluid densitometers operating on the acoustic resonance principle.

It is clearly important for the measured shift in frequency off a densitometer according to this invention, to be identifiable as closely as possible with the increase in mass represented by the sample. Extraneous frequency shifts should be minimized. Taking first the example of amplitude related effects, it is found that the linearity of the suspension system varies between commercially available loudspeakers. Preferably a loudspeaker or loudspeaker design is selected with a highly linear suspension system such that the resonant frequency remains constant over varying amplitudes of vibration. To compensate for less linear systems or to improve linearity still further, it is proposed to provide for electronic control of the amplitude of vibration. By, for example, the use of automatic gain control circuitry in the drive amplifier, a constant amplitude of vibration can be assured. Temperature changes can also result in an extraneous frequency shift. There is the possibility of thermal insulation of the suspension and steps can also be taken to direct Joule heat away from the coil or coils by, for example, filling the flux gap with a ferromagnetic material of high thermal conductivity. It is also preferable to operate the densitometer at low power levels to reduce further the problems of ohmic heating.

BRIEF DESCRIPTION OF THE DRAWINGS

The invention will now be described by way of examples only with reference to the accompanying drawings, in which:

FIG. 1 is a sectional view through part of a densitometer according to this invention;

FIG. 2 is a circuit diagram for the densitometer of FIG. 1;

DETAILED DESCRIPTION OF THE PREFERRED EMBODIMENTS

Figure 3:
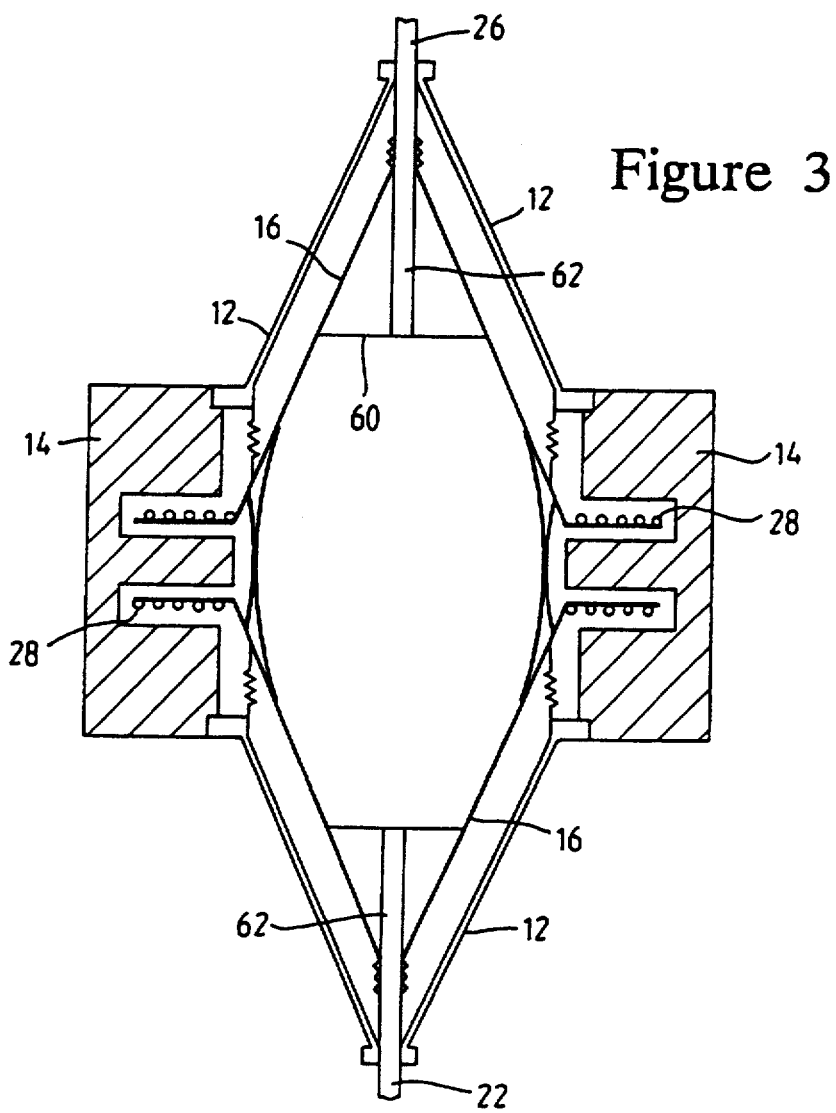
FIG. 3 is a view similar to FIG. 1, illustrating a modification.

Referring now to FIG. 1, a densitometer according to one embodiment of this invention comprises two loudspeakers connected together. The loudspeakers may be commercially available items but chosen according to strict criteria. The diaphragm is for example chosen to be chemically resistant to the sample in question and useful materials are PTFE, PVDF or stainless steel 316. The speaker has a high base resonant frequency since the effect of a fluid sample will be to reduce the frequency of resonance. Finally, the power dissipation of the transducer would be high enough to carry the mass loading associated with a fixed volume of sample having the maximum density with which the densitometer is required to operate. This would typically be a relative density of 2.7. Whilst the invention will operate with commercially available loudspeakers, it is preferable to use modified loudspeakers having particularly the diaphragms produced in a particular form suited to this invention.

Each loudspeaker has a base 10 including a speaker frame 12 and providing a mounting for a permanent magnet 14. The speaker diaphragms 16 are suspended through a peripheral ring suspension 18.

The two speaker diaphragms 16 are locked together about their entire periphery by bonding or clamping. Preferably, the diaphragms 16 are provided with a locking ring 20 such that the diaphragms move in unison and define a fixed sample volume. In an alternative arrangement, interlocking formations are provided on the respective diaphragms. The speaker frames 12 are suitable connected such that the original diaphragm suspensions 18 act in parallel to support the interconnected diaphragms. A sample inlet 22 is provided at the base of the densitometer communicating with the interior sample chamber 24 of the densitometer. Similarly, a sample outlet 26 is provided at the top of the densitometer.

The "voice" coils 28 of each of the two loudspeakers are of conventional form and, together with the detail of magnets 14 and suspensions 18, do not require further description. Within each loudspeaker, an impermeable shield 30 is provided to prevent the sample entering the voice coil. The coil leads (not shown) exit each diaphragm to the outside of the corresponding shield 30.

In operation, the densitometer is conveniently orientated vertically as shown in FIG. 1 with the sample being drawn through inlet 22 into the densitometer by means of a fixed displacement pump connected with the outlet 26. It may be desirable to provide a resilient mount to decouple the densitometer acoustically from its surroundings.

Turning now to FIG. 2, it can be seen that the coil 28 of one loudspeaker is connected in series with a potentiometer 40 to form a voltage input to an amplifier 42. The output of amplifier 42 is connected with variable RC network 44 providing a frequency corrected input to an audio frequency power amplifier 46 having its output connected to the coil 28 of the other loudspeaker. A capacitor 48 and resistor 50 connected in series across the two coils 28 serve to provide phase correction. A frequency meter 52 provides a measure of resonant frequency which can be used as described above to provide an indication of fluid density. The frequency meter can take the form of a counter gated by zero crossings of the signal and may be regarded as a period meter. The frequency meter may be microprocessor controlled to take a number of frequency measurements and provide an averaged result.

The power amplifier 46 is rated at 10 watts and provides a gain of 90DB. The response is flat over the range from DC to typically 20 kHz although lower limits will suffice in many applications.

In one example, apparatus according to FIG. 1 has a resonant frequency in air of 550 Hz. With the sample chamber 24 filled with distilled water, measured frequency drops to 350 Hz. With a test solution of sucrose with relative density of 1.98, the measured frequency drops further to 160 Hz. With a sample of unknown density the measured frequency is compared with such a predetermined frequency or range of frequencies to obtain a density value.

A modification will now be described with reference to FIG. 3 in which parts common to FIG. 1 retain the same reference numerals and will not be described further.

In this arrangement, a rigid sample container 60 is trapped between the opposing diaphragms 16. The inlet 22 and outlet 26 communicate with the sample container 60 through respective feeder tubes 62. There is no longer a need for the two diaphragms to be mechanically interlocked. The sample container will preferably be blow moulded from rigid light weight plastics material. With the arrangements of FIGS. 1 and 3, a particular known form of diaphragm suspension has been found to be especially well suited. In this, the suspension is formed integrally and contiguously with the diaphragm and comprises an annular "concertina" portion of the same material. This provides a high degree of stiffness which is found to be beneficial in the present invention.

Figure 4:
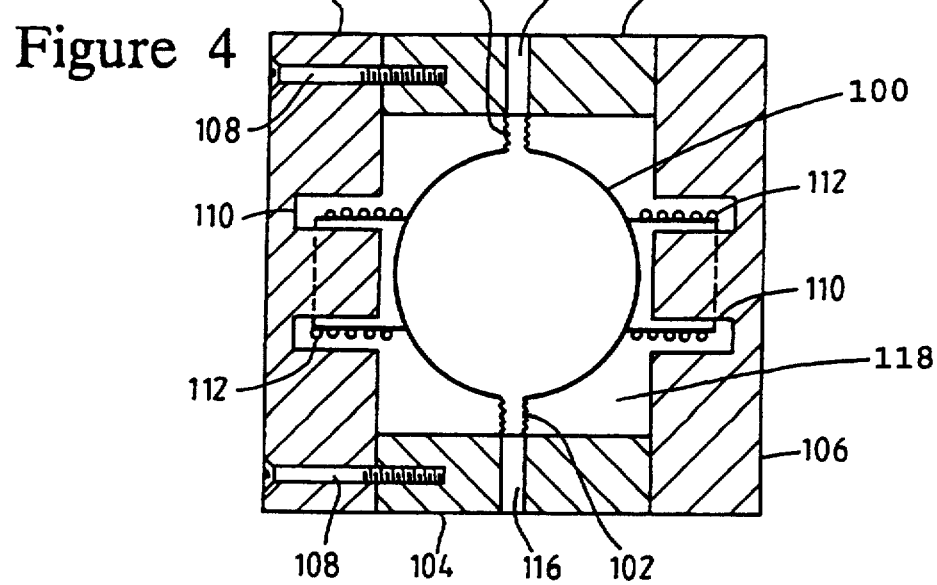
FIG. 4 is a sectional view through part of a further densitometer acording to this invention.

A further embodiment of this invention is illustrated in FIG. 4.

As with the previously described embodiments, this densitometer comprises two like "loudspeaker" elements joined in an opposing relationship. Each element comprises a dome-shaped diaphragm 100 mounted through annular suspension means 102 from a base in the form of a support sleeve 104. A disc shaped field magnet 106 is secured through screws 108 to the support sleeve 104 and a cylindrical recess 110 in the inner face of the field magnet accomodates a coil 112 formed integrally with the diaphragm 100.

The opposing "loudspeaker" element is identical and need not be described further.

The opposing diaphragms 100 define between them a spherical sample chamber 114 and inlet/outlet pipes 116 communicate between this sample chamber and the exterior of the densitometer. The void 118 between each diaphragm 100 and the opposing field magnet 106 may optionally be evacuated. Coil leads, not shown, extend from the coils 112 to the exterior of the densitometer for connection with electrical circuitry analogous to that shown in FIG. 2.

The manner of operation of the densitometer shown in FIG. 4 will be readily understood from the description of previous embodiments.

It has been explained that, preferably, steps are taken to ensure that the diaphragm or diaphragms of a densitometer according to the present invention, vibrate at constant amplitude. This can be achieved electronically and examples will be described with reference to FIGS. 5, 6 and 7.

Figure 5:
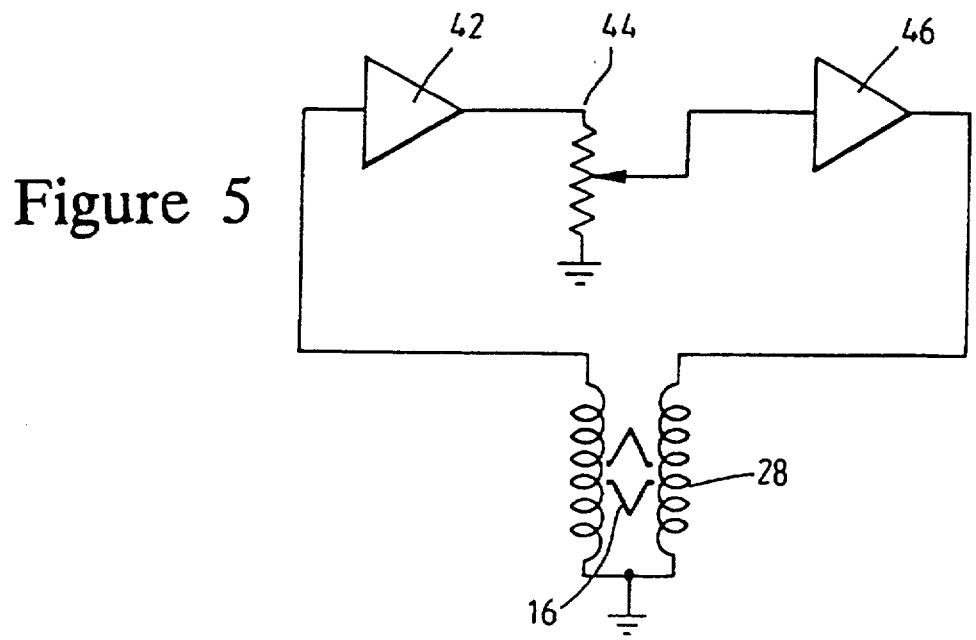
FIGS. 5, 6 and 7 are circuit diagrams illustrating alternative circuit arrangements for use in the densitometers of FIGS. 1, 3 or 4.
Figure 6:
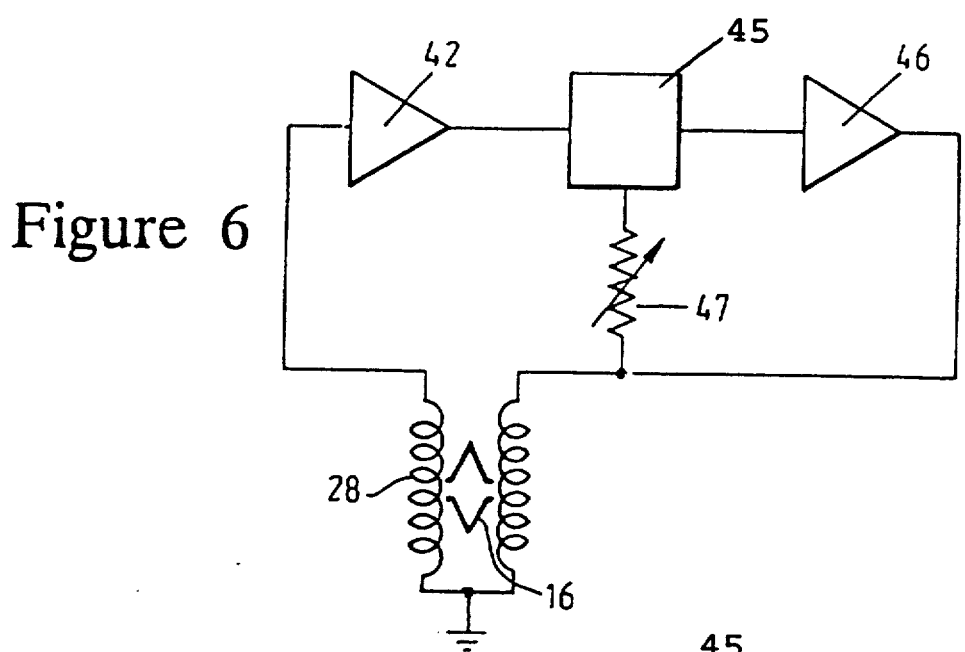
Figure 7:
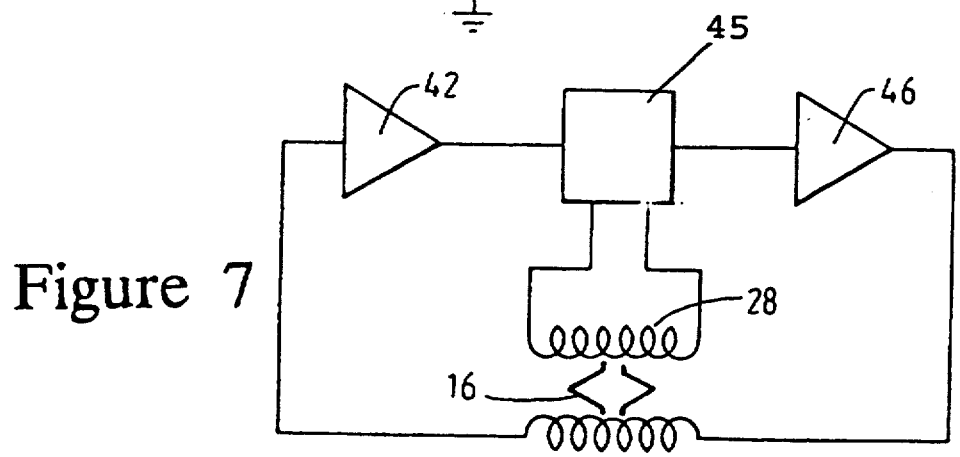

The circuits shown in FIGS. 5, 6 and 7 are in diagrammatic form and for reference, the drive circuit of FIG. 2 is represented at FIG. 5. Thus, corresponding ends of the coils 28 are earthed with the opposing end of one of the coils serving as the input for a first amplifier 42. The output of the first amplifier is taken through level setting potentiometer 44 to the input of a second amplifier 46 and the output of this amplifier 46 is connected with the second coil 28. It will be recognised that one of the coils is serving as a displacement sensor providing a positive feedback signal which is amplified at constant gain to provide an input to the other coil, which serves as a driver. Referring now to FIG. 6, the connection of coils 28 remains as before. However, the potentiometer 44 is replaced by an automatic gain control (AGC) unit 45. This receives a control input through a presettable resistor 47 connected with the output of amplifier 46. In this way, it is ensured that the amplitude of vibrational movement of the diaphragm remains constant.

In a modification, illustrated in FIG. 7, one coil 28 is connected in series between the output of amplifier 46 and the input of amplifier 42. The AGC unit 45 receives control inputs from the other coil 28. Again, the diaphragms are driven into resonance at constant amplitude.

It will be understood that a separate coil could be provided to provide an amplitude related signal to the AGC unit. Moreover, other feedback or compression arrangements could be provided to ensure that the amplitude of vibration remains constant despite changes in mass.

Figure 8:
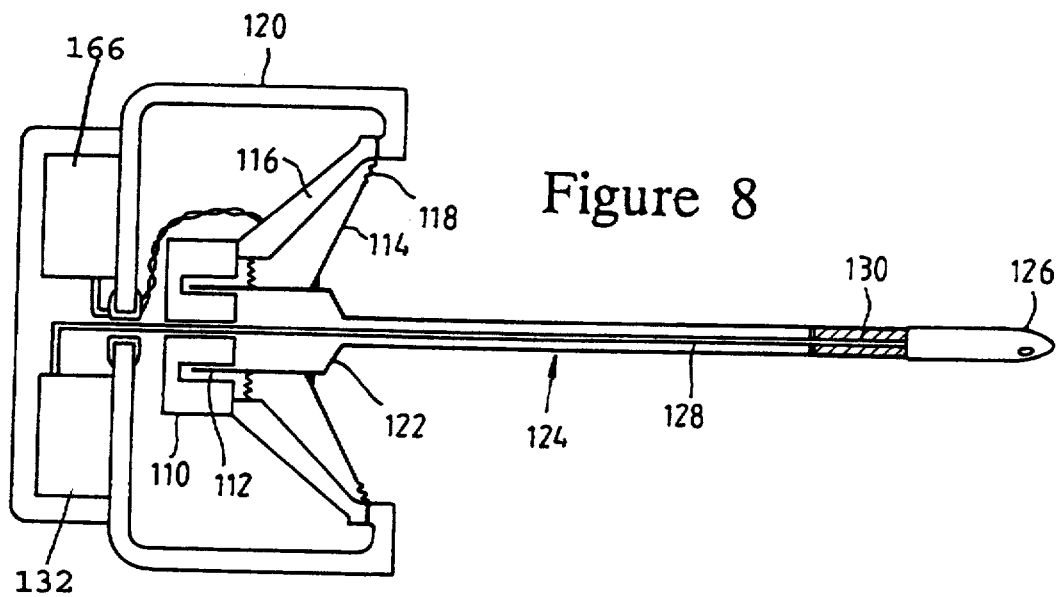
FIG. 8 is a sectional view through part of a further densitometer according to this invention.
Figure 9:
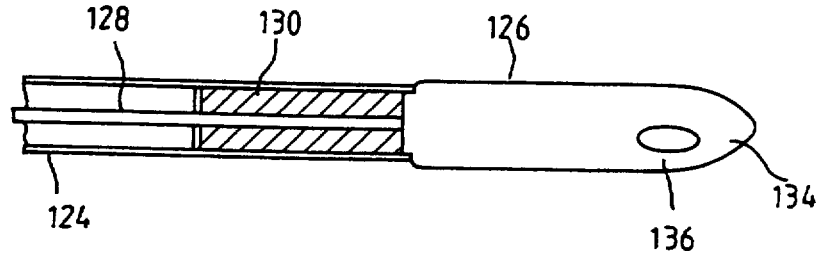
FIG. 9 is a part view, to an increased scale, showing the sample chamber of the densitometer of FIG. 8.

Referring now to FIGS. 8 and 9, a conventional loud speaker has a magnet 110, a coil 112, a diaphragm 114 through ring suspension 118 on a base formed from a spider 116 and a chassis 120. The loud speaker is of the form having a relatively small Mylar diaphragm. A stem holder 122 is bonded to the diaphragm 114 and coil 112 using an inelastic adhesive such as an epoxy resin or cyano-acrylic. This stem holder provides a mounting for a lightweight plastics tube 124 which carries at its free end a sample chamber 126. A thin pipe 128 extends the length of the tube 124 being supported at the end adjacent the sample chamber 126 by a plug 130 and, at the opposite end, extending through a bore in the magnet 110 to a fixed volume displacement pump shown diagrammatically at 132 and mounted within the chassis 120.

As seen best in FIG. 9, the sample chamber 126 has a coned forward end 134 and an inlet 136 provided to one side of the chamber.

Figure 10:
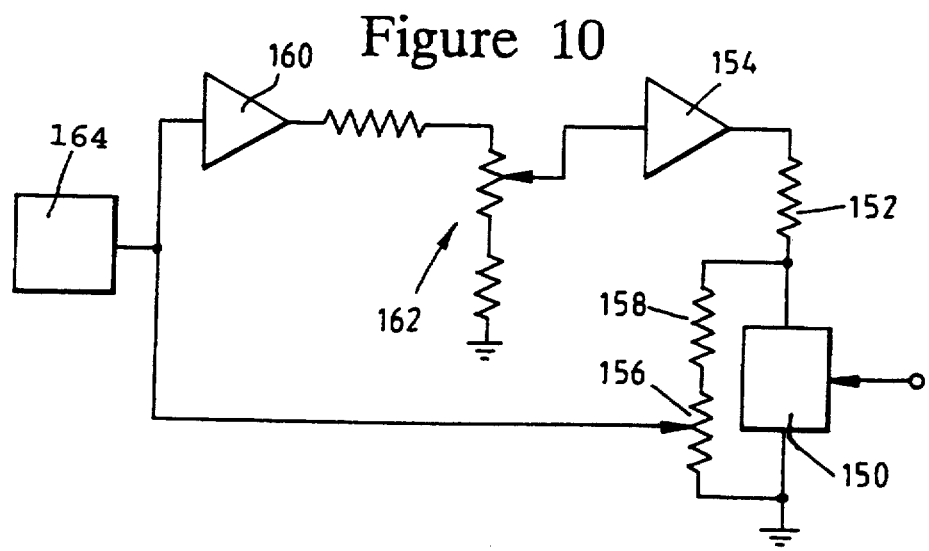
FIG. 10 is a circuit diagram for the densitometer of FIG. 8.

Referring now to FIG. 10, the electrical circuit diagram contains a diagrammatic representation at 150 of the parts shown in FIGS. 8 and 9. It will be seen that one coil terminal is connected to earth, whilst the other is connected through resistance 152 with the output of a power amplifier 154. Potentiometer 156 and resistor 158 are connected in parallel with the element 150, the wiper of the potentiometer 156 providing an input for a voltage amplifier 160. The output of the voltage amplifier 160 is taken through an attenuator network 162 to provide the input for power amplifier 154. A frequency meter shown diagrammatically 164 is connected to enable a determination to be made of the resonant frequency of vibration.

In the finished construction, the circuit elements of FIG. 10 are located within the chassis 166 shown in FIG. 8, at 166.

The densitometer is used by inserting the sample chamber 126 in a body of the sample fluid. By use of the fixed volume displacement pump 132, fluid is drawn into the test chamber 134 through the orifice 136. The volume is controlled so that the sample fluid does not enter the plug 130. An electrical determination is then made of the resonant frequency of the modified coil with the mass of the fluid contained within the test chamber being determined therefrom by reference to a calibration curve. In experiments carried out with a sucrose solution, it has been found that the described apparatus exhibits a linear relationship between resonant frequency and density. The characteristic can be simply expressed as:

$$p = \frac{t - k}{K}$$

where p=density, t=period of oscillation, k=resonance period in air and K=constant.

The cone formed at the forward end of the resonant chamber is important in reducing the effect on the measurement of viscosity. It is also important that the inlet 136 is provided at one side of the chamber or is alternatively of very small bore. If, in contrast, a large bore were provided at the forward end of the test chamber, no complete test volume would be defined on longitudinal oscillation of the test chamber. The use of the side entry into the test chamber is based on the fact that streamline flow will restrict sample exchange during test but permits good filling of the test volume.

The probe-like nature of this embodiment will be advantageous in certain applications. The vibration is, however, unlikely to be as uniform as with the previously described embodiments.

It should be understood that this invention has been described by way of examples only and a wide variety of modifications can be made without departing from the scope of the invention as set forth in the appended claims.

I claim:

1. A liquid densitometer comprising a base; a diaphragm suspended in the base for vibrational movement relative thereto; electromagnetic coupling means having cooperating elements mounted respectively on the base and the diaphragm and having an electrical terminal such that said vibrational movement of the diaphragm is excited on the application of a periodic electrical signal thereto; a positive feedback loop deriving an electrical signal representative of displacement of the diaphragm and applying said representative electrical signal to said electrical terminal to drive the diaphragm into vibrational resonance; a sample chamber for receiving a fixed volume of a liquid sample and associated with the diaphragm to load massively the diaphragm in accordance with the density of the sample; means for measuring the resonant frequency of vibration of the diaphragm and means for comparing said measured frequency with a predetermined frequency of vibration at a known massive loading of the diaphragm to obtain therefrom a measure of the density of the sample.

2. A densitometer according to claim 1, wherein said positive feedback loop includes automatic gain control to ensure vibration of the diaphragm at constant amplitude.

3. A densitometer according to claim 1, wherein the sample chamber is formed by a sample container carried on said diaphragm.

4. A fluid densitometer according to claim 1, comprising a further, like diaphragm opposed to said diaphragm to define a sample chamber therebetween.

5. A liquid densitometer comprising a base; a concave diaphragm; suspension means connected between the outer periphery of the diaphragm and the base to provide for generally axial vibrational movement of the diaphragm relative to the base; an electrical coil provided on the diaphragm; magnetic field means supported on the base and positioned to generate a magnetic field at the coil; displacement sensor means for applying an electrical signal representative of displacement of the diaphragm to the coil to excite said vibrational movement; a sample chamber for receiving a fixed volume of a fluid sample and associated with the diaphragm to load massively the diaphragm in accordance with the density of the sample; means electrically connected with said coil for measuring the resonant frequency of vibration of the diaphragm and comparison means for comparing said measured frequency with a predetermined frequency of vibration at a known massive loading of the diaphragm to obtain a measure of the density of the sample.

6. A liquid densitometer comprising a base; a diaphragm having a drive axis; annular suspension means disposed circumferentially of said drive axis and acting between the diaphragm and the base to provide for axial vibration of the diaphragm; a pair of coils provided on the diaphragm at respective opposite sides of the annular suspension means; magnetic field means supported on the base and positioned to generate a magnetic field at each of said coils; feedback means for detecting an electric signal from at least one of said coils; amplifier means connected to receive a feedback signal from said feedback means and connected with at least one of said coils to provide a drive signal thereto, the arrangement being such as to excite a resonant frequency of axial vibration of the diaphragm; a sample chamber for receiving a fixed volume of a fluid sample and associated with the diaphragm to load massively the diaphragm in accordance with the density of the sample; means electrically connected with at least one of said coils to determine the frequency of vibrational movement of the diaphragm and means for comparing said measured frequency with a predetermined frequency of vibration at a known massive loading of the diaphragm to obtain a measure of the density of the sample.

7. A fluid densitometer according to claim 6, wherein there is further provided gain control means associated with said amplifier means so as to provide for constant amplitude of vibrational movement of the diaphragm.

* * * * *